(12) United States Patent
Møller et al.

(10) Patent No.: US 8,608,709 B2
(45) Date of Patent: Dec. 17, 2013

(54) INJECTION DEVICE FOR APPORTIONING SET DOSES

(75) Inventors: Claus Schmidt Møller, Fredensborg (DK); Klaus Thøgersen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 726 days.

(21) Appl. No.: 11/664,950

(22) PCT Filed: Oct. 6, 2005

(86) PCT No.: PCT/EP2005/055068
§ 371 (c)(1),
(2), (4) Date: Aug. 5, 2009

(87) PCT Pub. No.: WO2006/040296
PCT Pub. Date: Apr. 20, 2006

(65) Prior Publication Data
US 2009/0299297 A1  Dec. 3, 2009

(30) Foreign Application Priority Data
Oct. 11, 2004  (EP) .................................... 04388068

(51) Int. Cl.
*A61M 5/00*  (2006.01)
(52) U.S. Cl.
USPC ........... 604/211; 604/207; 604/208; 604/198; 604/110; 604/192; 604/196
(58) Field of Classification Search
USPC ............ 604/196, 197, 192, 263, 164.08, 171, 604/110, 207–211, 198
See application file for complete search history.

(56) References Cited

U.S. PATENT DOCUMENTS

| | | | |
|---|---|---|---|
| 4,865,591 | A | 9/1989 | Sams |
| 5,320,609 | A | 6/1994 | Haber et al. |
| 5,505,704 | A | 4/1996 | Pawelka et al. |

(Continued)

FOREIGN PATENT DOCUMENTS

| | | |
|---|---|---|
| DE | 29703820 | 8/1998 |
| DE | 29724186 | 5/2000 |

(Continued)

OTHER PUBLICATIONS

International Search Report dated Jun. 23, 2006.

(Continued)

*Primary Examiner* — Kevin C Sirmons
*Assistant Examiner* — Edelmira Bosques
(74) *Attorney, Agent, or Firm* — Marc A. Began

(57) ABSTRACT

The invention concerns an injection device for apportioning set doses of a drug from a reservoir to a subject. The injection device comprises a dose setting member (20, 70) which is screwed out from the housing (30) to set a dose and pushed axially back to the housing (30) in order to expel the set dose. A scale drum (80) is axially and inrotatable coupled to the dose setting member (20, 70) such that the scale drum (80) is rotated up a thread (34) when the dose setting member (20, 70) is rotated to set a dose. When the dose setting member (20, 70) is pushed axially back to its initial position to inject the set dose, the scale drum (80) is released from its inrotatable connection in order to allow the scale drum (80) to rotate down the thread (34) and back to its zero position.

9 Claims, 5 Drawing Sheets

(56) References Cited

U.S. PATENT DOCUMENTS

| | | | |
|---|---|---|---|
| 6,004,296 A | 12/1999 | Steenfeldt-Jensen et al. | |
| 6,004,297 A * | 12/1999 | Steenfeldt-Jensen et al. | 604/207 |
| 6,048,336 A | 4/2000 | Gabriel | |
| 6,221,053 B1 * | 4/2001 | Walters et al. | 604/211 |
| 6,228,067 B1 | 5/2001 | Gabriel | |
| 7,291,132 B2 | 11/2007 | DeRuntz et al. | |
| 2002/0052578 A1 | 5/2002 | Moller | |
| 2002/0120235 A1 * | 8/2002 | Enggaard | 604/135 |
| 2004/0059299 A1 * | 3/2004 | Moller | 604/207 |
| 2005/0033244 A1 | 2/2005 | Veasey et al. | |

FOREIGN PATENT DOCUMENTS

| | | |
|---|---|---|
| DE | 10302163 | 7/2004 |
| EP | 295075 | 12/1988 |
| EP | 554995 A1 | 8/1993 |
| EP | 0937471 | 8/1999 |
| EP | 1000631 | 7/2002 |
| FR | 2684880 | 6/1993 |
| JP | H08-503874 A | 4/1996 |
| JP | 2002501790 | 1/2002 |
| WO | 9311813 | 6/1993 |
| WO | 9422507 A2 | 10/1994 |
| WO | 9839041 | 9/1998 |
| WO | WO 9938554 | 8/1999 |
| WO | 03075985 | 9/2003 |
| WO | 2004002557 | 1/2004 |
| WO | 2004078239 A1 | 9/2004 |
| WO | 2004078241 | 9/2004 |
| WO | WO 2004/078239 | 9/2004 |

OTHER PUBLICATIONS

Din ISO Pen-Systems—Part 1: Glass Cylinders for Pen-Injectors for Medical Use (ISO 13926-1:2004), Text in German and English 2005 (Opposition EP1827538 Dated May 7, 2010; Haselmeier/Novo Nordisk).

ISO Pen-Injectors for Medical Use—Part 1: Pen-Injectors—Requirements and Test Methods 2000, IST Edition, 12-15 (Opposition EP1827538 Dated May 7, 2010; Haselmeier/Novo Nordisk).

Ypsopen Leaflet Standard Cartridge (Opposition EP1827538 Dated May 7, 2013; Haselmeier/Novo Nordisk).

European Search Report issued in connection with counterpart European Application No. 05002872.9, mailed Jul. 27, 2005.

European Search Report issued in connection with counterpart European Application No. 05002998.2, mailed Aug. 18, 2005.

International Search Report and Written Opinion issued in connection with counterpart PCT Application No. PCT/EP2006/050800, mailed May 24, 2006.

International Preliminary Examination Report issued in connection with counterpart PCT Application No. PCT/EP2006/050800, mailed Aug. 23, 2007.

* cited by examiner

INJECTION DEVICE FOR APPORTIONING SET DOSES

CROSS-REFERENCE TO RELATED APPLICATIONS

This application is a 35 U.S.C. § 371 national stage application of International Patent Application PCT/EP2005/055068 (published as WO 2006/040296), filed Oct. 6, 2005, which claimed priority of European Patent Application 04388068.1, filed Oct. 11, 2004; this application further claims priority under 35 U.S.C. § 119 of U.S. Provisional Application 60/621,185, filed Oct. 22, 2004.

THE TECHNICAL FIELD OF THE INVENTION

The invention relates to an apparatus such as an injection pen for delivering a drug to the human body preferably in a subcutaneous way and especially to an injection device with a releasable scale drum.

DESCRIPTION OF RELATED ART

In the disclosure of the present invention reference is mainly made to the treatment of diabetes by injection of insulin; however this is only an exemplary use of the present invention.

Injection pens are mainly made for users who have to inject themselves frequently, e.g. people suffering from diabetes. A number of demands are set to such injection pens. The setting of a dose must be easy an unambiguous and it must be easy to read the set dose. It must be possible with a minimum of trouble to cancel or change a wrongly set dose and when the dose is injected the dose setting must return to zero. When a prefilled injection pen is in question, i.e. an injection pen which is disposed of when the reservoir is empty, the injection pen must further be cheap and made of materials suitable for recycling.

Most dose setting devices work with a threaded piston rod co-operating with a nut where the nut and the piston rod may be rotated relative to each other. The dose setting may be obtained by screwing the nut away from a stop to which it is return during injection by pressing the piston rod forward until the nut member abuts the stop. By other dose setting devices one of the elements, the nut or the piston rod, is kept inrotatable and the other is allowed to rotate a set angle depending on the set dose, whereby the piston rod is screwed forward a distance through the nut member.

In most injection devices for apportioning set doses it is preferred that the piston rod is constantly engaging the piston upon which it works during the injection thereby preventing back suction. To obtain this, precaution is taken to prevent the piston rod from moving backwards in a proximal direction.

A prior art delivery apparatus is disclosed in U.S. Pat. No. 6,004,297. This apparatus disclosed in FIG. 11-13 comprises a keyed guide for rotating the threaded piston rod such that the thread on the piston rod is screwed forward in a nut connected to the cartridge holder. The keyed guide is provided with a one-way ratchet mechanism interfaced between the keyed guide and the cartridge holder such that the keyed guide can only rotate in one direction relatively to the cartridge holder. The ratchet mechanism has an initial reluctance that must be overcome in order for the guide to rotate. This reluctance is set large enough to resist the torque exerted when rotating the dose setting knob meaning that only an adequate injection pressure exerted on the dose setting knob will overcome the reluctance and make the driver rotate. Further a scale drum is mounted inside the injection pen. The scale drum is supported by the dose setting member but is free to rotate relatively to the dose setting member and are forcedly rotated by an interior thread in the housing when axially moved. The set dose can be viewed through a window in the housing.

The tolerances in the thread connection between the scale drum and the housing is decisive for the precision of the display. If the scale drum were e.g. a little loose in the thread an erroneous dose size could be displayed, however if it were too tight in the tread connection, it would be difficult to press back the dose setting knob.

A similar injection pen is disclosed in WO 04/078239. This injection pen comprises a threaded piston rod which is screwed forward in an internal threaded nut when rotated. A drive sleeve having a thread mating the thread of the piston rod rotates the piston rod when moved axially forward. The drive sleeve is coupled to a dose dial sleeve which is rotated to dial up a dose. The dose dial sleeve is rotated out from the housing in order to set up a dose and it is rotated back to release the set dose. The drive sleeve is rotated together with the dose dial sleeve when a dose is set but prevented form rotation when the set dose is injected.

In use, the dose dial sleeve is rotated out of the housing when a dose is set and it is rotated in the opposite direction when the dose dial sleeve is pressed back to inject the set dose. Thereby the markings on the dose dial sleeve indicating the dose size becomes visible to the user as the dose dial sleeve is screwed out of the housing. Should a user accidentally disturb the rotation of the dose dial sleeve when injecting a dose e.g. by applying a sideway pressure to the dose dial sleeve this would add to the force needed to press back the dose dial sleeve.

Another injection pen is disclosed in U.S. Pat. No. 6,221,053. In this injection pen the injection button is integral with the scale drum and is rotated up or down a thread provided on the exterior of a driver to set a dose. In order to inject the set dose, the combined injection button and scale drum is pushed back in an axial non-rotatable movement which forces the driver to rotate. Since the driver has an internal thread mating the thread on the keyed piston rod, the keyed piston rod is moved forward through the key available in the nut member inside the housing. Since the scale drum is not rotated during injection a window stretching all 360 degrees of the pen is provided. A second window provided in the driver indicates the set dose.

In this solution, the scale indications are visible over all the 360 degrees that the window stretches. The user most therefore be particular observant to read the set dose through the extra window provided in the driver.

The piston rod drive disclosed in U.S. Pat. No. 6,004,297 and in U.S. Pat. No. 6,221,053 basically comprises two elements. A first element which mates the keyed piston rod and a second element with an inner thread mating the outer thread of the piston rod. The piston rod is screwed forward when the first element and the second element are relatively rotated.

In U.S. Pat. No. 6,004,297, the first element is the piston rod guide mating the keyed piston rod and the second element is the threaded nut member which makes the piston rod rotate forward during injection. Whereas in U.S. Pat. No. 6,221,053, the first element is the keyed nut member inrotatable connected to the housing and the second element is the threaded driver. In the latter case, the piston rod is brought forward without rotating.

Some drugs, such as insulin are self-administered, and the typical diabetes person will require subcutaneous injections of insulin several times during the course of the day. Since most injections of these drugs are performed in private surroundings by the user himself there is a great desire for very simple yet also very precise injection devices.

DESCRIPTION OF THE INVENTION

Having regard to the above-identified prior art devices, it is an object of the present invention to provide a drug delivery device which eliminates disadvantages in the prior art drug delivery device and provides a more precise display of the set dose.

Correspondingly, an injection device is provided where the scale drum is inrotatable connected to the dose setting member such that whenever the dose setting member is screwed out from the housing, the scale drum follows this rotation one to one without any slippage. When the dose setting member is brought axially back to its initial position, the scale drum must however be able to rotate in order to return to a zero setting. This is accomplished by providing a releasable coupling by which the scale drum can be released from its inrotatable connection with the dose setting member.

By the inrotatable coupling between the scale drum and the dose setting member any slack between these two elements is avoided when setting a dose and by the axial returning of the dose setting member it is assured that no rotating parts can be accessed by the user during injection.

In an exemplary embodiment the scale drum is guided in a thread with a very little diameter which limits the loss of energy during injection. As the driving thread between the dose setting member and the piston rod guide all ready has a little diameter, it is to be preferred that the thread guiding the scale drum also has a little diameter.

The support tube guiding the scale drum can either be made integral with the housing e.g. through injection moulding or it can be made as a separate member inrotatable connected to the housing.

In a different exemplary embodiment, the releasable coupling is provided between outwardly pointing teeth on the dose setting member and a toothed ring provided on the interior surface of the scale drum. Both the outwardly pointing teeth and the toothed ring has a relatively small width of e.g. 2 to 5 mm such that the coupling is released when the dose setting member and the scale drum is axially moved e.g. 2 to 5 mm in relation to each other.

The scale drum and the dose setting member must therefore be able to move axially in relation to each other in order to release the toothed engagement.

Instead of making the scale drum and the dose setting member able to move axially in relation to each other, the dose setting member can be divided into two parts. A first part which is connected to the push button and a second part which is axially connected to the scale drum such that this second part and the scale drum follow each other in a one to one relationship in the axial direction.

The releasable coupling is in this embodiment provided between the first dose setting member and the scale drum. When the first dose setting member is moved axially in relation to the second dose setting member and the scale drum, the inwardly pointing teeth provided on the first dose setting member slides out of engagement with the toothed ring provided on the inside surface of the scale drum and the scale drum is free to rotate in relation to both the first dose setting member and the second dose setting member as these members are moved in the axially in the distal direction.

In a further exemplary embodiment a shield is provided between the push button and the housing. The shield is inrotatable but slidable mounted in the housing. At its proximal end the shield is coupled to the push button through a disconnectable coupling such that the push button can be either rotatable connected or rotatable disconnected to the shield.

The disconnectable coupling is preferably made from a number of teeth provided on the proximal end of shield engaging similar teeth provided inside the push button such that the push button is connected when a predetermined pressure is applied to the proximal end of the push button and disconnected when no or only little pressure is applied.

In one example of how an embodiment of the present invention may constructed, an injection device as shown in the figures is adapted for apportioning set doses of a drug from a reservoir. The device comprises a housing (30), a piston rod (40) having a not circular cross-section (42) and an outer thread (41), a piston rod drive (50, 60), which itself comprises two components: A) a first drive element (50, 60) mating the not-circular cross section (42) of the piston rod (40), and B) a second drive element (50, 60), which has an inner thread (53) mating the thread (41) of the piston rod (40). A dose setting and injection mechanism is included and comprises a dose setting member (20, 70) coupled to the piston rod drive (50, 60) through a thread connection (63, 73) along which the dose setting member (20, 70). The dose setting member is screwed out of the device by a distance determined by the angle of rotation. The threaded connection of the dose setting member (63, 73) causes axially movement back into the device to be transformed into rotational motion. The scale drum 80 is, in this example, supported by the dose setting member (20, 70). In this embodiment a scale element (80) is rotatably connected to the dose setting member (20, 70) through a releasable coupling (23, 83) such that the scale element (80) in one position of a releasable coupling (23, 83) follows rotation of the dose setting member (20, 70) and in a different position is rotatable released from the dose setting member (20, 70). The piston rod 40 rotates.

DEFINITIONS

An "injection pen" is typically a mechanical i.e. user energized injection apparatus having an oblong or elongated shape somewhat like a pen for writing. Although such pens usually have a tubular cross-section, they could easily have a different cross-section such as triangular, rectangular or square.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
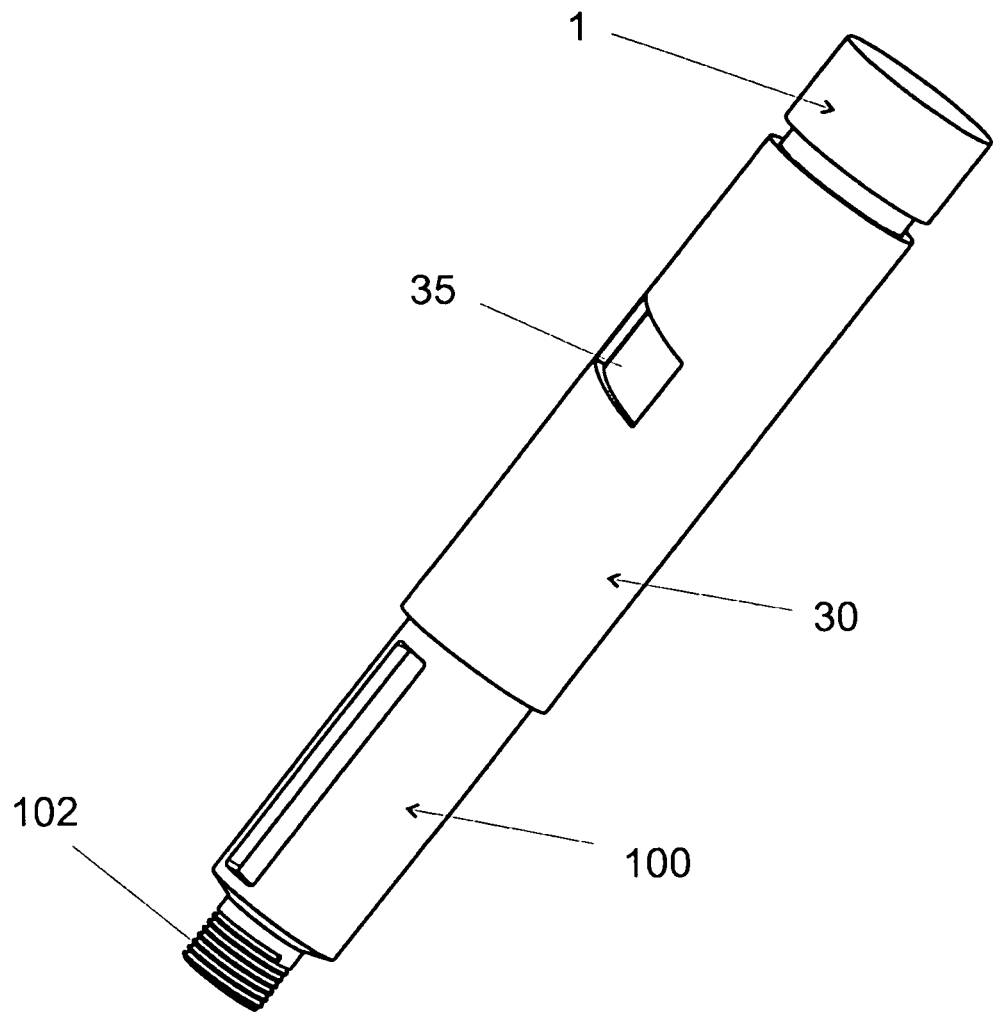
FIG. 1 shows a perspective view of the injection device.
Figure 2:
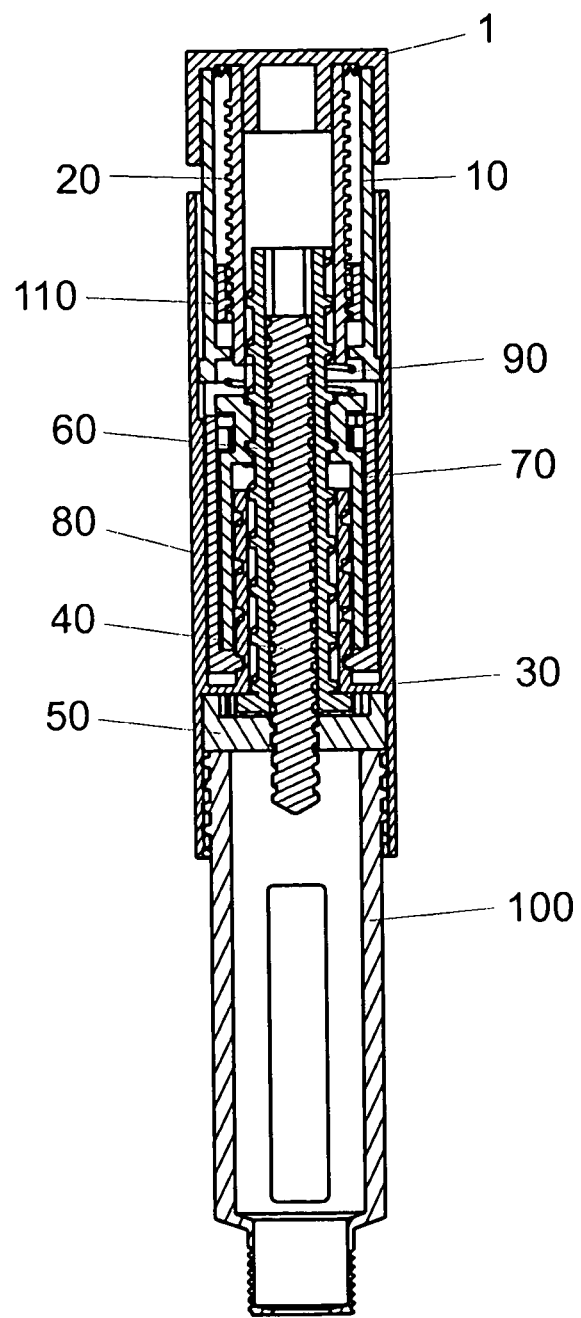
FIG. 2 shows a sectional view of the injection device with no dose set.
Figure 3:
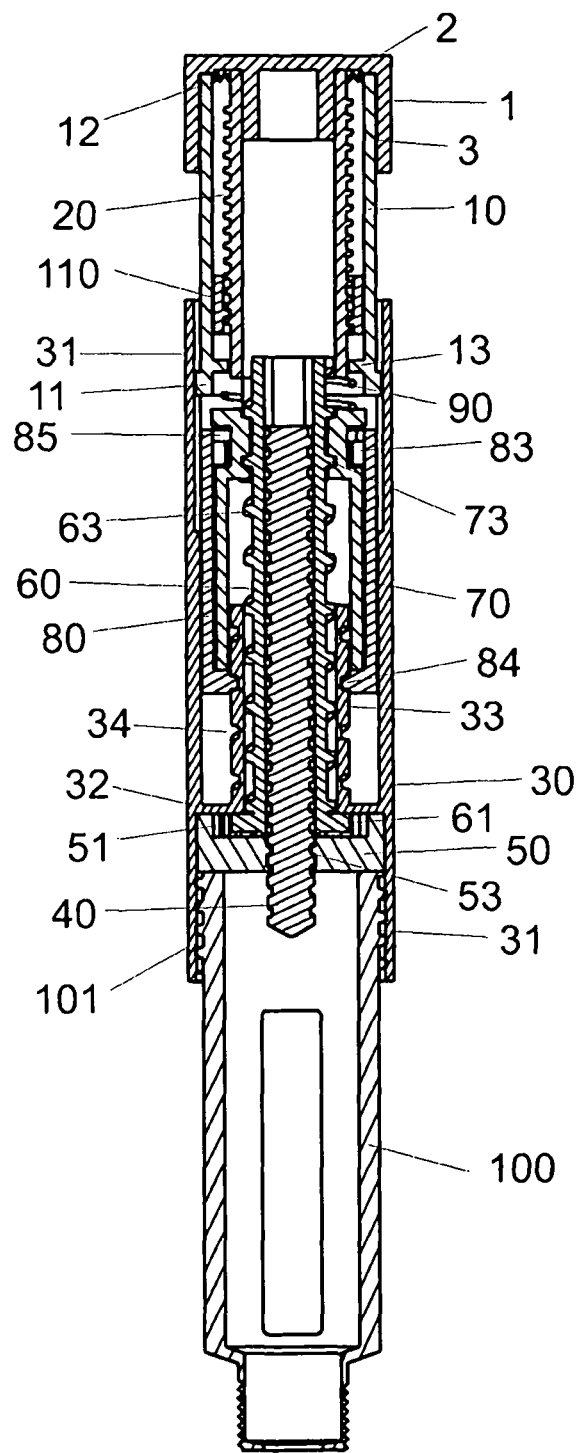
FIG. 3 shows a sectional view of the injection device with a dose set.
Figure 4:
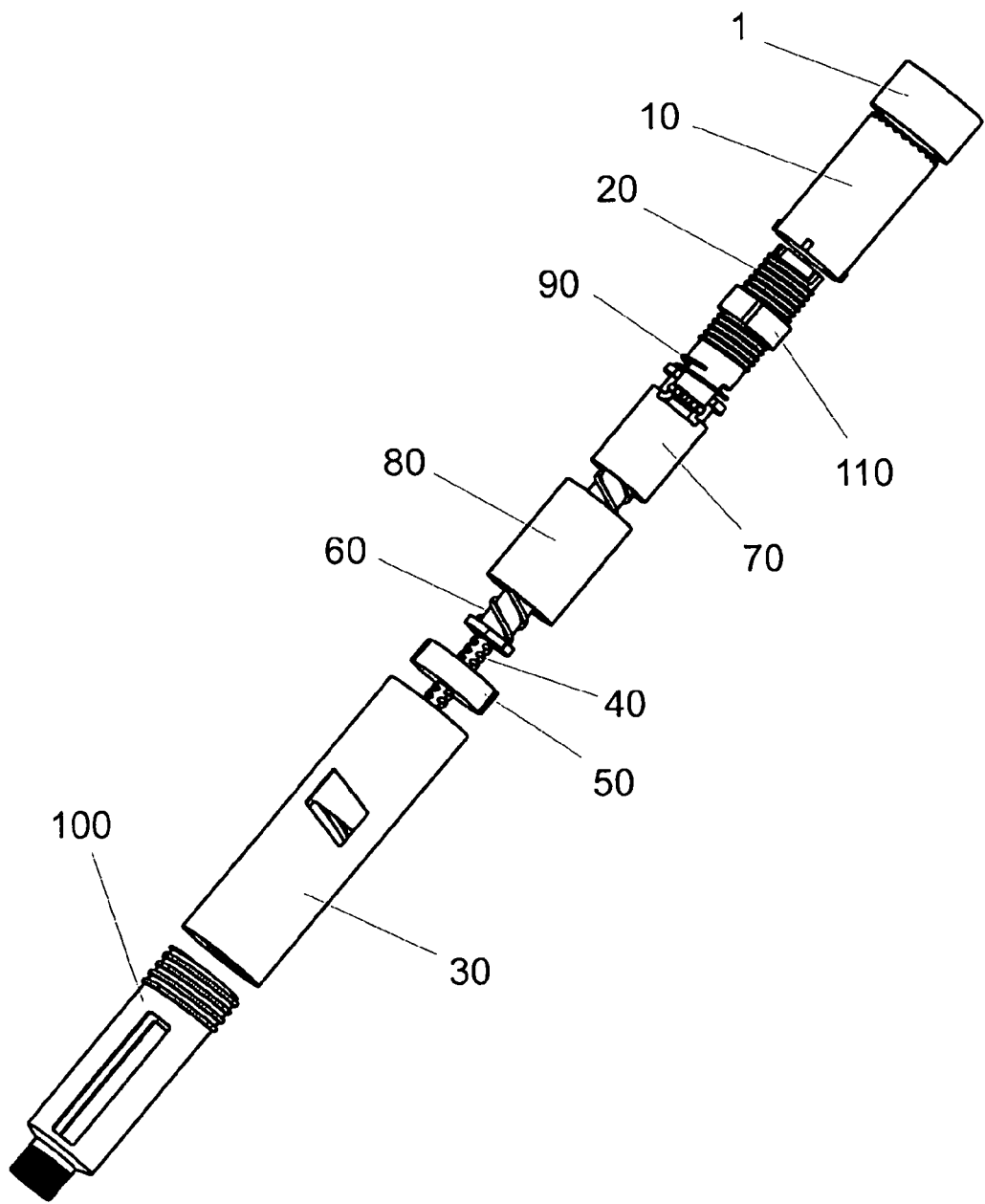
FIG. 4 shows a partly exploded view of the injection device.
Figure 5:
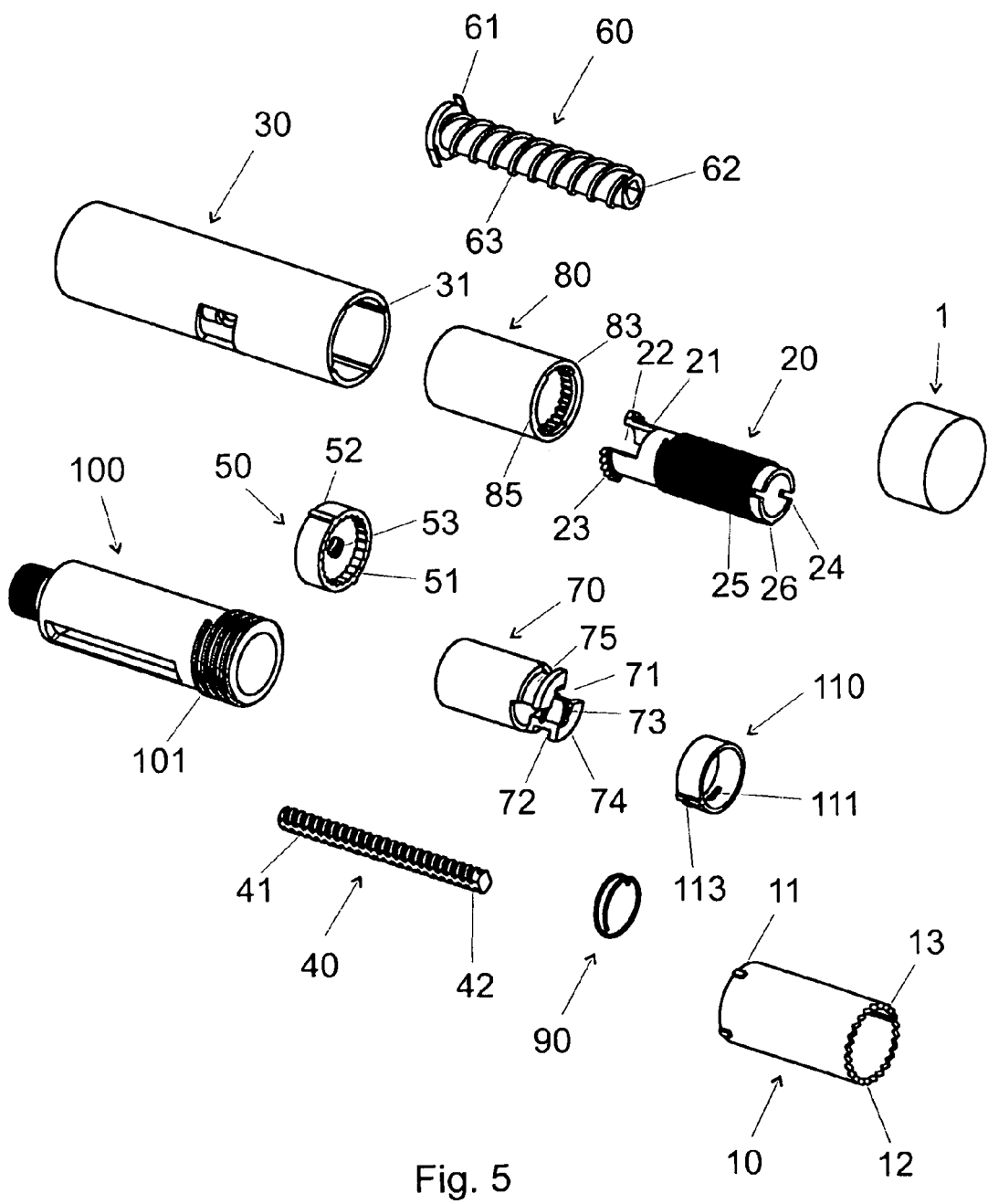
FIG. 5 shows a perspective view of the parts presented in FIG. 4.

FIG. 1 discloses a user energized injection pen comprising a housing 30 and a cartridge holder 100. The housing 30 is provided with a window 35 through which the dose set by rotating the dose setting button 1 can be viewed. The cartridge holder 100 is at its distal end provided with a thread 102 for securing an injection needle to the injection pen.

The interior of the injection pen is detailed disclosed in FIG. 2 to 5.

The push button 1 is provided at the proximal end of the injection device and connected to a first dose setting member 20 by a plurality of not shown protrusions entering slits 24 in the proximal end of the first dose setting member 20. The inside surface of the skirt 3 of the push button 1 is supported by the outside surface of a shield 10 in a rotatable manner.

The first dose setting member 20 is rotatable connected to a second dose setting member 70. The first dose setting member 20 is located at the proximal end of the injection pen and the second dose setting member is located downstream in the distal direction.

The shield 10 is axially slidable in the housing 30 but rotational locked to the housing 30 by the protrusion 11 sliding in the track 31. A rim of shield teeth 12 on the proximal end of the shield 10 interact with a corresponding rim of push button teeth 2 provided on the inside of the push button 1. The push button 1 is able to rotate relatively to the shield 10 when no pressure is applied to the push button 1, but when pressure is applied e.g. during injection, the interaction between the push button teeth 2 and the shield teeth 12 locks the push button 1 rotational to the shield 10. When the injection button 1 is rotated relatively to the shield 10 a clicking sound is produced by the push button teeth 2 sliding over the shield teeth 12. The number of push button teeth 2 and shield teeth 12 is preferably such that one click is heard for each International Unit of insulin dialled.

The housing 30 has an inwardly pointing flange 32 carrying a support tube 33 pointing in the proximal direction. The inwardly pointing flange 32 is shown as moulded integral with the housing 30 but could be a separate part inserted in the housing 32. The support tube 32 is on its outside i.e. pointing towards the inside of the housing 30, provided with a support thread 34. This support thread 34 is engaged by a corresponding thread 84 located on the interior side of the scale drum 80.

A piston rod 40 is centrally located in side the housing 30. The piston rod 40 has a piston rod thread 41 mating a nut thread 53 inside a nut 50 and a key 42 (creating a non-circular cross-section) mating an interior key 62 in a piston rod guide 60 such that the piston rod 40 is screwed forward in the nut 50 when the piston rod guide 60 is rotated. The nut 50 is inrotatable fastened to the housing 30 through a number of raised portions 52 engaging a number of not shown slits on the interior surface of the housing 30.

A ratchet mechanism 51, 61 located between the nut 50 piston rod guide 60 works as a one-way coupling. The piston rod guide 60 is at its distal end provided with at least one pawl 61 which engages a rim of nut teeth 51 provided inside the nut 50. The nut teeth 51 and pawl 61 interactions prevents the piston rod guide 60 from rotating in a direction screwing the piston rod 40 backwards in the injection device. In the disclosed embodiment, the prohibited direction is counter clockwise.

The piston rod guide 60 is on its exterior side provided with a guide thread 63 mating the interior thread 73 of second dose setting member 70 making it possible to screw the second dose setting member 70 up and down the piston rod guide 60.

The second dose setting member 70 is rotational coupled to the first dose setting member 20 by the flanges 21 on distal end of the first dose setting member 20 engaging the slots 71 on the proximal end of the second dose setting member 70. Furthermore the flanges 72 on the second dose setting member 70 enters into slots 22 on the first dose member 20 thereby preventing the first dose setting member 20 from rotating relatively to the second dose setting member 70.

The flanges 21 on the distal end of the first dose setting member 20 is provide with outwardly pointing teeth 23 able to engage an interior ring of drum scale teeth 83 provided inside the scale drum 80.

Further, the proximal end of the second dose setting member 70 provides a platform 74 for a spring 90. The opposite end of the spring 90 rest against a distal collar 13 located on the interior side of the shield 10 so urging the shield 10 and the second dose setting member 70 in opposite directions.

The distal side of the platform 74 forms a neck 75 which secures the drum scale teeth 83 of the scale drum 80 making the scale drum 80 a slave to the second dose setting member 70 i.e. the scale drum 80 follows the axial movement of the second dose setting member 70.

Since the second dose setting member 70 and the scale drum 80 are axially coupled together the spring 90 could rest on the proximal end of the scale drum 80 instead of the platform 74 of the second dose setting member 70.

As the shield 10 is urged in the proximal direction by the spring 90 so is the injection button 2 which is connected to the first dose setting member 20. The rim of outwardly pointing teeth 23 is locked against movement in the proximal direction by the flange 85 on the scale drum 80 such that the first dose setting member 20 retains its position despite the pressure from the spring 90.

The spring 90 separates the first dose setting member 20 and the second dose setting member 70 a distance larger than the height of the push button teeth 2 and the shield teeth 12 such that when the first dose setting member 20 is pressed against the second dose setting member 70 thereby moving the outwardly pointing teeth 23 out of engagement with the drum scale teeth 83, the push button teeth 2 will engage the shield teeth 12 thereby preventing the first dose setting member 20 from rotating relatively to the shield 10.

In order to set a dose the user holds the housing 30 and rotates the push button 1 in the clockwise direction. The first dose setting member 20 rotates simultaneous and forces the second dose setting member 70 to rotate due to the interaction between the flanges 71 and the flanges 21. The outwardly pointing teeth 23 on the first dose setting member 20 engages the teeth 83 on the scale drum 80 which makes the scale drum 80 rotate in the clockwise direction as well.

The now rotational locked first dose setting member 20, second dose setting member 70 and scale drum 80 is rotated up the support thread 34 on the support tube 33 by the interior thread 84 inside the scale drum 80. The second dose setting member 70 rotates up the guide thread 63 which has the same pitch as the support thread 34. The scale drum 80 abuts the second dose setting member 70 at its distal end thereby forcing the second dose setting member 70 up the guide thread 63.

The not shown markings on the scale drum 80 can be viewed through an opening 32 in the housing 30 preferably equipped with a magnifier.

The injection button 1 can be rotated in both directions; in the first direction the size of the dose is increased as the first dose setting member 20, the second dose setting member 70 and the scale drum 80 is rotated up the support thread 34. In the opposite direction, the first dose setting member 20, the second dose setting member 70 and the scale drum 80 is dialled down the support thread 34 thereby lowering the set dose.

When an adequate dose has been set, the user expels the set dose by pressing the injection button 2 back to its initial position in an axial movement.

The teeth 2 on the injection button 1 engages the teeth 12 on the shield 10 which is rotational locked to the housing 30 thereby preventing the first dose setting member 20 from rotating relatively to the housing 30.

When the first dose setting member 20 is moved axially until the outwardly pointing teeth 23 stands on the proximal end of the slots 71, the releasable coupling between the scale drum 80 and the first dose setting member 20 is released. Further pressure on the injection button 1 brings both the first dose setting member 20 and the second dose setting member 70 forward. This axial and non-rotational forward movement forces the piston rod guide 60 to rotate in the clockwise direction due to the engagement between the guide rod thread 63 and the interior thread 73 of the second dose setting member 70.

Rotation of the piston rod guide 60 forces the piston rod 40 to rotate also in the clockwise direction and to be screwed forward in the thread 53 of the nut 50.

Since the drum scale 80 is locked in the neck 75 and guided in the support thread 34 it rotates back to its initial position. This rotation occurs in the counter clockwise direction.

A nut 110 is located over the first dose setting member 20 and is in threaded contact with an exterior thread 25 on the first dose setting member 20 through an internal thread 111. The nut 110 is at the same time inrotatable connected to the shield 10 by the protrusion 113 being guided in the longitudinal slot 13 located on the inside of the shield 10.

When a dose is set the first dose setting member 20 is rotated relatively to the shield 10 and to the nut 110 bringing the nut 110 forward in the distal direction from a proximal starting point. The distance the nut 110 is brought forward relates to the size of dose being set.

When the set dose is injected, the nut 110 is moved axially forward the same distance as the first dose setting member 20 and the shield 10. The position of the nut 110 on the exterior thread 25 therefore relates to the remaining content of drug in the reservoir.

When the nut 110 reaches the distal end 26 of the thread 25 which end 26 is parallel to a longitudinal axis of the injection device, the nut 110 can be screwed no further and the first dose setting member 20 in prohibited from further rotation. A more detailed description of such end-of-dose feature is provided in WO 01/019434 which is hereby incorporated by reference.

Some preferred embodiments have been shown in the foregoing, but it should be stressed that the invention is not limited to these, but may be embodied in other ways within the subject matter defined in the following claims.

The invention claimed is:

1. An injection device for apportioning set doses of a drug from a reservoir comprising a housing (30), a piston rod (40) having a not circular cross-section (42) and an outer thread (41) a piston rod drive (50, 60) comprising; a first drive element (50, 60) mating the not-circular cross section (42) of the piston rod (40), a second drive element (50, 60), which has an inner thread (53) mating the thread (41) of the piston rod (40), a dose setting and injection mechanism comprising a dose setting member (20, 70) coupled to the piston rod drive (50, 60) through a thread connection (63, 73) along which the dose setting member (20, 70) by rotation is screwed out from the proximal end of the housing (30) a distance determined by the angle of rotation during the setting of a dose and wherein the thread connection (63, 73) transforms an axial movement of the dose setting member during expulsion of a dose into a rotation of one of the first or second drive elements (50, 60) relative to the other, and wherein a scale drum is axially supported by the dose setting member (20, 70), characterized in that, the scale drum element (80) further is rotatably connected to the dose setting member (20, 70) through a releasable coupling (23, 83) such that the scale drum (80) in one position of a releasable coupling (23, 83) follows rotation of the dose setting member (20, 70) and in a different position is rotatable released from the dose setting member (20, 70), and wherein during setting of a dose the scale drum (80) is coupled to the dose setting member and wherein during dose administration the scale drum is decoupled.

2. An injection device according to claim 1, characterized in that, the scale drum (80) has an interior thread (84).

3. An injection device according to claim 2, characterized in that, the interior thread (84) on the scale drum (80) is coupled to a support thread (34) provided on the exterior surface of a support tube (32) encompassed in the housing (30).

4. An injection device according to claim 1, characterized in that, a support tube (32) is structurally connected to the housing (30).

5. An injection device according to claim 1, characterized in that, the releasable coupling (23, 83) is provided between drum scale teeth (83) on the scale drum (80) and outwardly pointing teeth (23) on the dose setting member (20, 70) which teeth (23, 83) can be axially disengaged.

6. An injection device according to claim 1, characterized in that, the dose setting member (20, 70) comprises a first dose setting member (20) and a second dose setting member (70) which is rotatable connected and axially displaceable relatively to each other.

7. An injection device according to claim 6, characterized in that, the first dose setting member (20) is coupled to a proximal push button (1).

8. An injection device according to claim 1, characterized in that, a shield (10) is provided between a push button (1), which shield (10) is axially and non-rotatable guided in the housing (30).

9. An injection device according to claim 8, characterized in that, a number of push button teeth (2) in the push button (1) rides over a number of shield teeth (12) provided at the proximal end of the shield (10) when the push button (1) and the first dose setting member is rotated relatively to the shield (10) and the housing (30) to set a dose, wherein the piston rod rotates during injection of medication to screw toward an injecting end of the device.

\* \* \* \* \*